(12) United States Patent
Chen et al.

(10) Patent No.: US 11,466,301 B2
(45) Date of Patent: Oct. 11, 2022

(54) NUCLEOTIDE TRIPHOSPHATE IMMOBILISED ON A SUPPORT AND THEIR USE IN NUCLEIC ACID SYNTHESIS

(71) Applicant: Nuclera Nucleics Ltd., Cambridge (GB)

(72) Inventors: Michael Chen, Cambridge (GB); Jiahao Huang, Cambridge (GB); Radu Lazar, Cambridge (GB); Gordon McInroy, Cambridge (GB)

(73) Assignee: Nuclera Nucleics Ltd., Cambridge (GB)

( * ) Notice: Subject to any disclaimer, the term of this patent is extended or adjusted under 35 U.S.C. 154(b) by 371 days.

(21) Appl. No.: 16/480,128

(22) PCT Filed: Jan. 26, 2018

(86) PCT No.: PCT/GB2018/050220
§ 371 (c)(1),
(2) Date: Jul. 23, 2019

(87) PCT Pub. No.: WO2018/138508
PCT Pub. Date: Aug. 2, 2018

(65) Prior Publication Data
US 2019/0338331 A1  Nov. 7, 2019

(30) Foreign Application Priority Data
Jan. 27, 2017  (GB) ..................... 1701396

(51) Int. Cl.
| | |
|---|---|
| *C12P 19/34* | (2006.01) |
| *C07H 1/02* | (2006.01) |
| *C07H 19/10* | (2006.01) |
| *C07H 19/20* | (2006.01) |
| *C40B 50/04* | (2006.01) |
| *C40B 50/18* | (2006.01) |
| *C40B 80/00* | (2006.01) |

(52) U.S. Cl.
CPC ................ *C12P 19/34* (2013.01); *C07H 1/02* (2013.01); *C07H 19/10* (2013.01); *C07H 19/20* (2013.01); *C40B 50/04* (2013.01); *C40B 50/18* (2013.01); *C40B 80/00* (2013.01)

(58) Field of Classification Search
CPC ....... C12P 19/34; C12Q 1/6804; C07H 19/10; C07H 19/20; C40B 50/04; C40B 50/18; C40B 80/10
See application file for complete search history.

(56) References Cited

U.S. PATENT DOCUMENTS

| | | | | |
|---|---|---|---|---|
| 5,990,300 A | * | 11/1999 | Hiatt ..................... | C07H 19/10 536/25.3 |
| 2016/0046974 A1 | | 2/2016 | Efcavitch et al. | |
| 2016/0108382 A1 | | 4/2016 | Efcavitch et al. | |

FOREIGN PATENT DOCUMENTS

WO  2016/128731 A1  8/2016

OTHER PUBLICATIONS

International Search Report issued in corresponding International Patent Application No. PCT/GB2018/050220 dated May 15, 2018.
Hogg et al., "Promiscuous DNA synthesis by human DNA polymerase & thetas," Nucleic Acids Research, 40: 2611-2622 (2011).
Written Opinion issued in corresponding International Patent Application No. PCT/GB2018/080220 dated May 15, 2018.

\* cited by examiner

*Primary Examiner* — Jezia Riley
(74) *Attorney, Agent, or Firm* — Morgan, Lewis & Bockius LLP (57) ABSTRACT

The invention relates to methods of synthesizing polymers, biopolymers, and nucleic acids, to immobilised dNTP/NTPs and kits comprising said immobilised dNTP/NTPs for use in said methods of nucleic acid synthesis.

19 Claims, 6 Drawing Sheets

Surface patterned with square features of immobilized dNTPs; four colours represent four bases. Representation depicts three tracks of nine features for depiction only.

Solution (depicted as circular droplet) containing addition biocatalyst and free initiator strand (length N) addressed to pattern features. Strand of length N+1 is formed, and is immobilised to the surface.

Following washing, a droplet containing addition biocatalyst is dispensed over feature 1. Cleavage condition is applied to feature one to release the N+1 strand, which is then moved to feature 2.

NUCLEOTIDE TRIPHOSPHATE IMMOBILISED ON A SUPPORT AND THEIR USE IN NUCLEIC ACID SYNTHESIS

FIELD OF THE INVENTION

The invention relates to methods of synthesizing polymers, biopolymers, and nucleic acids, to immobilised dNTP/NTPs and kits comprising said immobilised dNTP/NTPs for use in said methods of nucleic acid synthesis.

BACKGROUND OF THE INVENTION

Nucleic acid synthesis is vital to modern biotechnology. The rapid pace of development in the biotechnology arena has been made possible by the scientific community's ability to artificially synthesize DNA, RNA and proteins.

Artificial DNA synthesis—a £1.8 billion and growing market—allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. DNA synthesis is currently, and has historically, been implemented as solid-phase synthesis. Solid-phase synthesis is a method where the target molecule/biopolymer is synthesised in a stepwise fashion whilst immobilised on a solid support. The solid support may be a surface, a bead, or some other insoluble material. Notably, throughout the process the progressing molecule/biopolymer remains immobilised on the solid support, until synthesis is complete and the molecule/biopolymer is harvested. Robert Bruce Merrifield won the Nobel Prize in 1984 for the invention of solid-phase peptide synthesis, which presented the concept for solid-phase DNA synthesis.

Solid-phase synthesis offers some advantages over solution-phase synthesis. The nascent molecule/biopolymer may be exposed to a reagent or reagents necessary for a reaction to occur, and then washed to remove excess reagent(s). This washing provides efficient and thorough purification, while minimising product loss, in a reduced time frame when compared to many other purification strategies.

However, a key drawback to solid-phase synthesis is the retention of nascent molecules/biopolymers that have not successfully reacted. In the case of solid-phase DNA synthesis, this may be a nascent DNA strand that has not successfully undergone an N to N+1 conversion upon exposure to a phosphoramidite/activator solution (chemical synthesis) or a nucleotide triphosphate/biocatalyst solution (enzymatic synthesis). Two methods are commonly used to avoid this situation occurring: (1) The nascent DNA strand is exposed to a large excess of reagent, to increase N to N+1 conversion rates; and (2) a capping step is employed following the N to N+1 conversion, to permanently cap, and thus prevent any further reactions, any remaining N length strands. Nevertheless, despite optimisation over several decades, the problem of heterogeneous product pools following synthesis remains. This manifests as a target product of length X containing X-1, X-2, ..., X-N species, which are undesirable and challenging to remove during purification.

WO 2015/159023 describes an alternative method of nucleic acid synthesis. WO 2016/034807 describes a modified nucleotide for use in nucleic acid synthesis. US 2016/0108382 describes methods for identifying polymerases, such as modified terminal nucleotidyl transferases (TdT), that are capable of binding nucleotides comprising removable 3'-O-blocking moieties to a nucleic acid initiator, without the use of a template. U.S. Pat. No. 8,808,989 describes methods for synthesizing polynucleotides. U.S. Pat. Nos. 7,541,444 and 7,785,796 describe modified nucleotide and nucleoside molecules. S. M. Minhaz Ud-Dean (2008) Syst Synth Biol. 2(3-4), 67-73 describes a theoretical model for template-free synthesis of long DNA sequence. http://2015.igem.org/Team:Cooper_Union/DeNovoSynthesis describes a DNA synthesis method using terminal deoxynucleotidyltransferase (TdT).

There is therefore a need to provide improved methods of nucleic acid synthesis that are able to overcome the problems associated with currently available methods.

SUMMARY OF THE INVENTION

According to a first aspect of the invention, there is provided an alternating-phase polymer synthesis method which comprises the steps of:
(a) providing a monomer immobilised to a support moiety via a cleavable linker;
(b) providing a polymer of length (N);
(c) providing components to couple the polymer to the immobilised monomer to create an immobilised, coupled polymer of length (N+1);
(d) removing any uncoupled polymers; and
(e) cleaving the immobilised, coupled polymer of length (N+1) from the support moiety.

According to a second aspect of the invention, there is provided a nucleic acid synthesis method which comprises the steps of:
(a) providing a deoxynucleotide triphosphate (dNTP) or nucleotide triphosphate (NTP) immobilised to a support moiety via a cleavable linker;
(b) providing an initiator nucleic acid sequence of length (N);
(c) adding a nucleic acid synthesis catalyst to couple the initiator nucleic acid sequence to the immobilised dNTP/NTP to create an immobilised, coupled sequence of length (N+1);
(d) removing any uncoupled initiator nucleic acid sequences; and
(e) cleaving the immobilised, coupled sequence of length (N+1) from the support moiety.

According to a third aspect of the invention, there is provided a nucleic acid synthesis method which comprises the steps of:
(a) providing a deoxynucleotide triphosphate (dNTP) or nucleotide triphosphate (NTP) immobilised to a support moiety via a cleavable linker;
(b) providing an initiator nucleic acid sequence of length (N);
(c) providing a nucleic acid trap strand sequence which is complimentary to, and capable of hybridising to, the initiator nucleic acid sequence, wherein said trap strand is immobilised at the 3'-end to the same support moiety as the dNTP/NTP in step (a);
(d) adding a nucleic acid synthesis catalyst to couple the initiator nucleic acid sequence to the immobilised dNTP/NTP to create an immobilised, coupled sequence of length (N+1);

(e) providing a reaction temperature greater than the melting temperature of any trap strand/initiator sequence duplexes;
(f) removing any uncoupled initiator nucleic acid sequences;
(g) providing a reaction temperature lower than the melting temperature of any trap strand/initiator sequence duplexes;
(h) cleaving the immobilised, coupled sequence of length (N+1) from the support moiety; and
(i) providing a reaction temperature greater than the melting temperature of any trap strand/initiator sequence duplexes to separate the trap strand/initiator sequence duplexes.

According to a fourth aspect of the invention, there is provided a nucleic acid synthesis method which comprises the steps of:
(a) providing a deoxynucleotide triphosphate (dNTP) or nucleotide triphosphate (NTP) immobilised to a mobile phase support moiety via a cleavable linker;
(b) providing an initiator nucleic acid sequence of length (N) immobilised to a solid phase support moiety via a cleavable linker;
(c) adding a nucleic acid synthesis catalyst to couple the mobile phase immobilised dNTP/NTP to the solid phase immobilised initiator nucleic acid sequence to create an immobilised, coupled sequence of length (N+1);
(d) removing any uncoupled initiator nucleic acid sequences; and
(e) cleaving the mobile phase support moiety from the immobilised, coupled sequence of length (N+1).

According to a further aspect of the invention, there is provided an immobilised dNTP/NTP of formula (I):

wherein $R_1$ and $R_2$ independently represent H or OH or a protected derivative thereof;
X represents hydrogen or one or more phosphate groups;
W represents a base;
Y represents a cleavable linker; and
Z represents a support moiety.

According to a further aspect of the invention, there is provided the use of an immobilised dNTP/NTP as defined herein in a nucleic acid synthesis method.

According to a further aspect of the invention, there is provided a nucleic acid synthesis kit which comprises an immobilised dNTP/NTP as defined herein, an initiator nucleic acid sequence as defined herein, a nucleic acid synthesis catalyst as defined herein and instructions to use said kit in accordance with any of the methods defined herein.

DETAILED DESCRIPTION OF THE INVENTION

General Alternating-Phase Process

According to a first aspect of the invention, there is provided an alternating-phase polymer synthesis method which comprises the steps of:
(a) providing a monomer immobilised to a support moiety via a cleavable linker;
(b) providing a polymer of length (N);
(c) providing components to couple the polymer to the immobilised monomer to create an immobilised, coupled polymer of length (N+1);
(d) removing any uncoupled polymers; and
(e) cleaving the immobilised, coupled polymer of length (N+1) from the support moiety.

It will be appreciated that greater than one monomer may be added by providing the product of step (e) to an additional monomer immobilised to a support moiety and then repeating steps (b) and (e) until a polymer of desired length is synthesised.

In one embodiment, the components in step (c) comprise any suitable coupling enzyme.

In one embodiment, the removing in step (d) comprises a washing step. Such a washing step serves the purpose of providing an error correction step by removing all unbound polymers.

In one embodiment, the cleaving in step (e) comprises light, pH, temperature, voltage and the like.

In one embodiment, an isolation or capture step is conducted following step (e).

It will be appreciated that the polymer may either be in solution phase or is itself immobilised to a support moiety via a cleavable linker.

An example protocol of how the method of the first aspect of the invention may be performed is described as follows and may be seen in FIG. 3:

Alternating-Phase Synthesis

1. A reagent (e.g., a monomer of a polymer) is immobilized to support moiety 1 via a cleavable linker. The reagent can be a dNTP or NTP or another monomer unit.
2. A nascent polymer of length N (e.g., a single-stranded DNA initiator strand) is introduced to the reagent immobilized to support moiety 1 from step (1). The nascent polymer is either in solution phase or is itself immobilized to support moiety 2. If necessary to couple the nascent polymer to the monomeric reagent immobilized to the support moiety 1, a catalyst is introduced with the nascent polymer (e.g., an enzyme). This step thus creates N+1 polymers coupled to support moiety 1.

3. Any uncoupled nascent polymers of length N are removed, for example by washing.
4. All N+1 polymers are cleaved from support moiety 1 and captured.
5. N+1 polymers from step (4) are introduced to another immobilized monomeric reagent repeating step (2)-(5).
6. Steps (2)-(5) are repeated until a polymer of desired composition and length is created.

Alternating-Phase Nucleic Acid Synthesis Process

Figure 3:
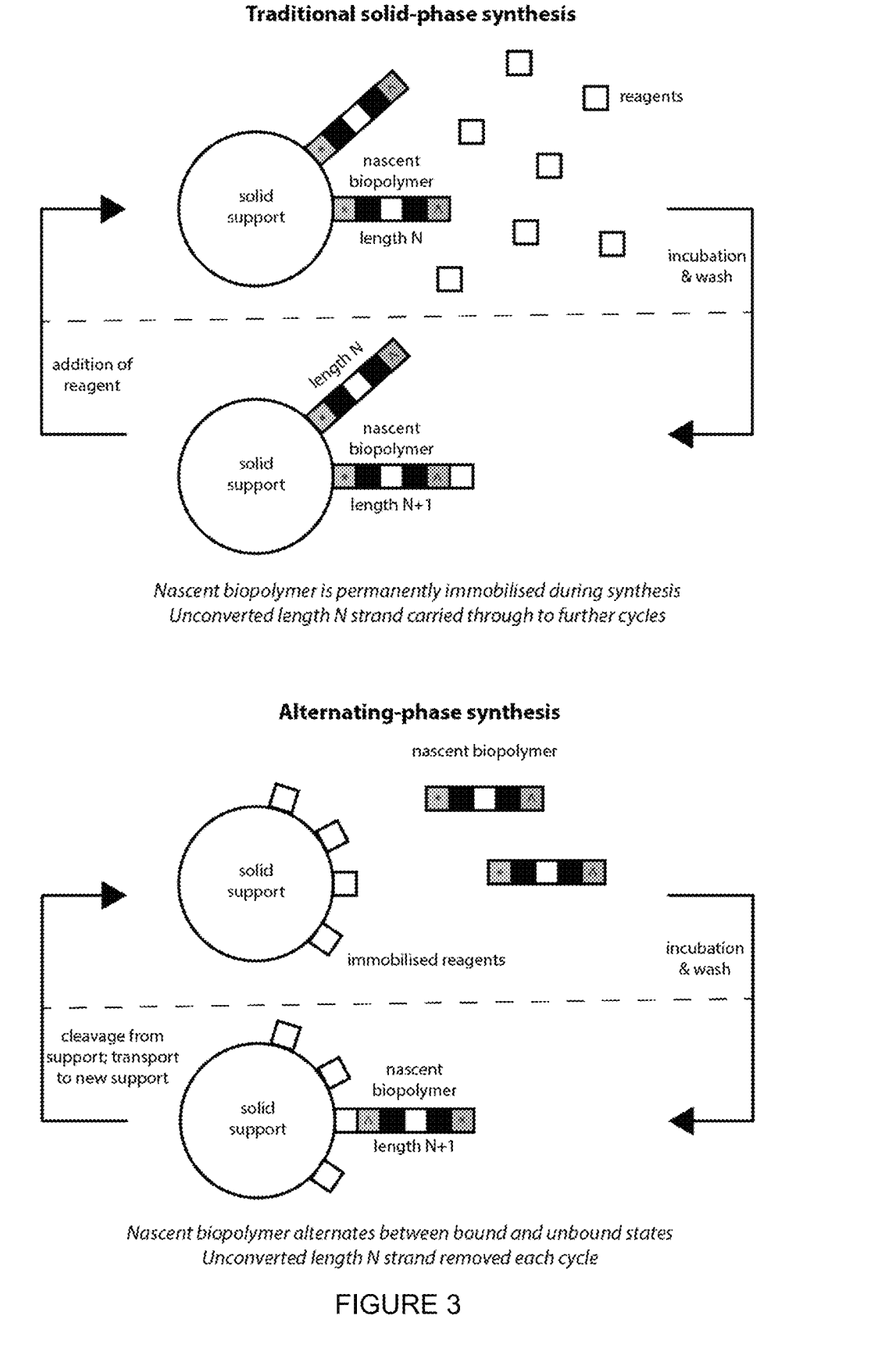
FIG. 3: Solid-phase synthesis vs. alternating-phase synthesis.

One embodiment of the general alternating-phase process described herein as the first aspect of the invention is referred to herein as "Alternating-Phase Nucleic Acid Synthesis Process" which is also described in FIG. 3.

In one embodiment of the first aspect of the invention, the monomer is a deoxynucleotide triphosphate (dNTP) or nucleotide triphosphate (NTP) immobilised to a support moiety via a cleavable linker.

In one embodiment of the first aspect of the invention, the polymer is an initiator nucleic acid sequence of length (N).

In one embodiment of the first aspect of the invention, the coupling components comprise a nucleic acid catalyst such as an enzyme (e.g. terminal deoxynucleotidyl transferase (TdT), poly (U) polymerase, poly (A) polymerase and polymerase theta (PolQ) or phophoramidite.

Thus, according to a second aspect of the invention, there is provided a nucleic acid synthesis method which comprises the steps of:
(a) providing a deoxynucleotide triphosphate (dNTP) or nucleotide triphosphate (NTP) immobilised to a support moiety via a cleavable linker;
(b) providing an initiator nucleic acid sequence of length (N);
(c) adding a nucleic acid synthesis catalyst to couple the initiator nucleic acid sequence to the immobilised dNTP/NTP to create an immobilised, coupled sequence of length (N+1);
(d) removing any uncoupled initiator nucleic acid sequences; and
(e) cleaving the immobilised, coupled sequence of length (N+1) from the support moiety.

It will be appreciated that greater than one dNTP/NTP may be added by providing the product of step (e) to an additional deoxynucleotide triphosphate (dNTP) or nucleotide triphosphate (NTP) immobilised to a support moiety and then repeating steps (b) and (e) until a nucleic acid of desired length is synthesised.

In one embodiment, the removing in step (d) comprises a washing step. Such a washing step serves the purpose of providing an error correction step by removing all unbound initiator nucleic acid sequences.

In one embodiment, the cleaving in step (e) comprises light, pH, temperature, voltage and the like.

In one embodiment, an isolation or capture step is conducted following step (e).

The method described herein has significant advantages, in particular in respect to nucleic acid synthesis. For example:

(A) Error Correction: Eliminating X-1 Species

The key advantage of the alternating-phase DNA synthesis methodology of the present invention over conventional solid-phase DNA synthesis is the avoidance of contaminating X-1, X-2, etc. ... species, as any strands which fail the N to N+1 conversion are not immobilised and thus washed away at the point of their occurrence. Coupling failure resulting in X-1, X-2, etc. ... species represents the largest source of error in phosphoramidite solid phase synthesis and is avoided via alternating-phase DNA synthesis (see Ma et al (2012) Trends in Biotechnology 30(3), 147).

(B) Error Correction: Controlled Exposure to Reagent

By virtue of immobilizing the reagent (e.g., immobilizing the purine or pyrimidine moiety of a nucleotide triphosphate), unintended additional reactions of the nascent biopolymer with reagent resulting in insertions is made impossible. In the case of enzymatic DNA synthesis where DNA synthesis is controlled by large sterically-blocking moieties attached to the purine or pyrimidine of the nucleotide triphosphate (as proposed in U.S. Pat. No. 8,808,989), more than one of these modified nucleotide triphosphates may add onto the nascent DNA strand.

Figure 1:
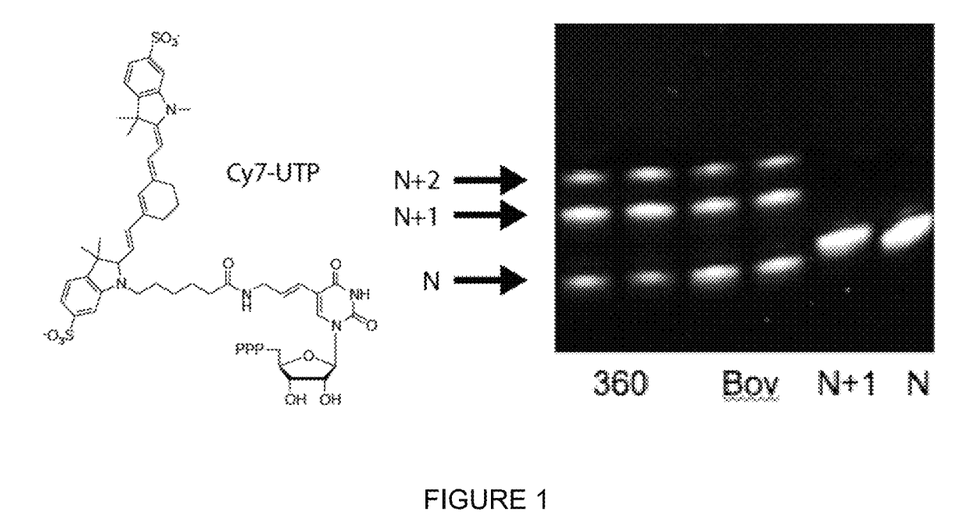
FIG. 1: TdT variants labelled 360 and Bov add multiple Cy7-UTPs to an initiator strand with length N.

The fact that TdT is able to add multiple nucleotide triphosphates with large sterically-blocking moieties attached to the purine or pyrimidine moiety is well known to those skilled in the art (see Berdis and McCutcheon (2007) ChemBioChem 8(12), 1399-1408), and in fact is a widely used strategy for 3'-end labeling DNA with nucleotide triphosphates containing detectable tags (e.g., biotin, fluorescent dyes, other functional groups). An example of 3'-end labeling is shown below with the addition of multiple Cy7-UTPs to DNA strands N nucleotides long.

The addition of multiple nucleotides, as shown in FIG. 1, defeats the ability of the user to add one specific nucleotide at a time to a nascent DNA strand. Thus, forming de novo user-defined DNA sequences in this manner is impossible.

On the other hand, after the addition of an immobilized nucleotide triphosphate to a nascent DNA strand, no additional nucleotide is available for reaction. Thus, controlled addition of one nucleotide per cycle is made possible.

(C) Avoiding Polymerase Steric Gate Clashes

The polymerase steric gate is a steric mechanism polymerases and transferases use to discriminate between nucleotide triphosphates with differing 2' and 3' substituents (see Joyce (1997) PNAS 94(5), 1619-1622). For example, many DNA polymerases discriminate against ribonucleotide triphosphates by sterically blocking the 2'-OH.

Figure 2:
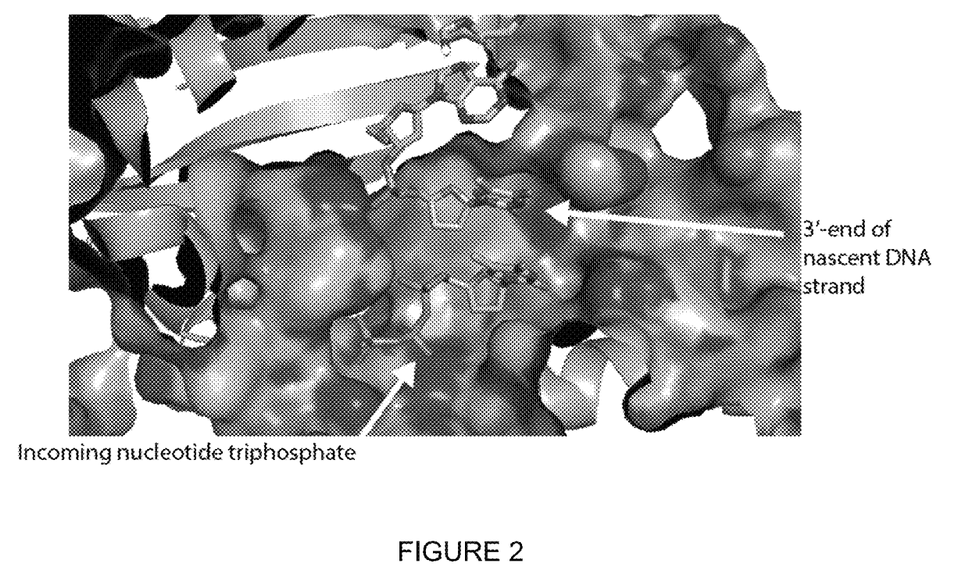
FIG. 2: View of TdT active site (PDB ID: 4127). The sugar moiety of the incoming nucleotide fits tightly into the active site whereas the nitrogenous base is not sterically hindered.

In the specific case of TdT, the steric gate of TdT makes it difficult to engineer TdT to accept large 2' or 3' modifications (see WO 2016/139477). The steric gate of TdT is made obvious by the crystal structure of murine TdT (PDB ID: 4127) in complex with a nascent DNA strand and an incoming nucleotide triphosphate, as shown in FIG. 2. The protein is represented in FIG. 2 as a solvent-excluded surface and the nucleic acid represented as ball-and-stick. Clearly, fitting in additional 2' or 3' modifications for reversible termination is challenging given the tightness of fit between the sugar moiety of the incoming nucleotide and the protein surface.

On the other hand, there is ample room for large base modifications. For this reason, immobilization of nucleotide triphosphates by the base (e.g., the purine or pyrimidine moiety) is of industrial utility because of the ease with which polymerases like TdT accept nitrogenous base modifications.

Example protocols of how the method of the second aspect of the invention may be performed are described as follows and may be seen in FIG. 3:

Alternating-Phase Synthesis with Nucleic Acid

1. A nucleotide or nucleoside activated for coupling (e.g., a 5'-n-phosphate group where n represents 1 or more phosphates or a 2', 3', or 5'-O-phosphoramidite) is immobilized to support moiety 1 via the purine or pyrimidine moiety through a cleavable linker.
2. A nascent nucleic acid of length N (e.g., a single-stranded DNA initiator strand) is introduced to the reagent immobilized to support moiety 1 from step (1). The nucleic acid is either in solution phase or is itself immobilized to support moiety 2 via the 5'- or 3'-end. If necessary to couple the nucleic acid to the nucleotide 5'-triphosphate immobilized to support moiety 1, a catalyst is introduced with the nucleic acid (e.g., an enzyme). This step thus creates N+1 polymers coupled to support moiety 1. In the case of 5'-O-dimethoxytrityl nucleoside phosphoramidites under anhydrous conditions, an acid to deprotect the dimethoxytrityl (DMT) protecting group must be introduced every cycle to allow for phosphoramidite coupling.

3. Any uncoupled nucleic acids of length N are removed, for example by washing.
4. All N+1 nucleic acids are cleaved from the solid support and captured.
5. N+1 nucleic acids from step (4) are introduced to another immobilized nucleotide 5'-triphosphate repeating step (2)-(5).
6. Steps (2)-(5) are repeated until a nucleic acid of desired composition and length is created.

Immobilized dNTP/NTP De Novo Alternating-Phase Nucleic Acid Enzymatic Synthesis

1. Support moiety 1 is immobilized with dNTP/NTPs (e.g., dATP/ATP or dTTP/UTP or dCTP/CTP or dGTP/GTP). The dNTP/NTPs are immobilized support moiety, for instance through a cleavable linker to the nitrogenous base (e.g., purine or pyrimidine moiety).
2. A solution containing an addition biocatalyst (e.g., terminal deoxynucleotidyl transferase (TdT) or poly (U) polymerase) and initiator strand (of length N) is introduced to the immobilized dNTP/NTP reagent.
3. The addition biocatalyst catalyzes formation of a covalent bond between the 3'-terminus of the unbound initiator and the immobilized dNTP/NTP, resulting in growth of the initiator strand by one nucleotide in the 3' direction (i.e., formation of an N+1 species).
4. Further dNTP/NTP addition to the N+1 species is precluded by virtue of immobilization through the terminal unit to support moiety.
5. The immobilized N+1 species is washed with a wash solution to remove any uncoupled initiator strands as an error correction step.
6. The immobilized N+1 species are treated with a condition that cleaves the immobilized N+1 species from the surface. The condition could be light, pH, temperature, voltage etc. If continuing de novo nucleic acid synthesis, the process moves to step (7). If terminating de novo nucleic acid synthesis, the process moves to step (8).
7. The addition biocatalyst and cleaved N+1 species are introduced to another immobilized dNTP/NTP support moiety that has not been exposed to solution from step (2). The immobilized dNTP/NTPs identity would be that desired for subsequent incorporation into the growing strand. Steps (2)-(8) are repeated until the desired sequence is achieved.

Figure 7:
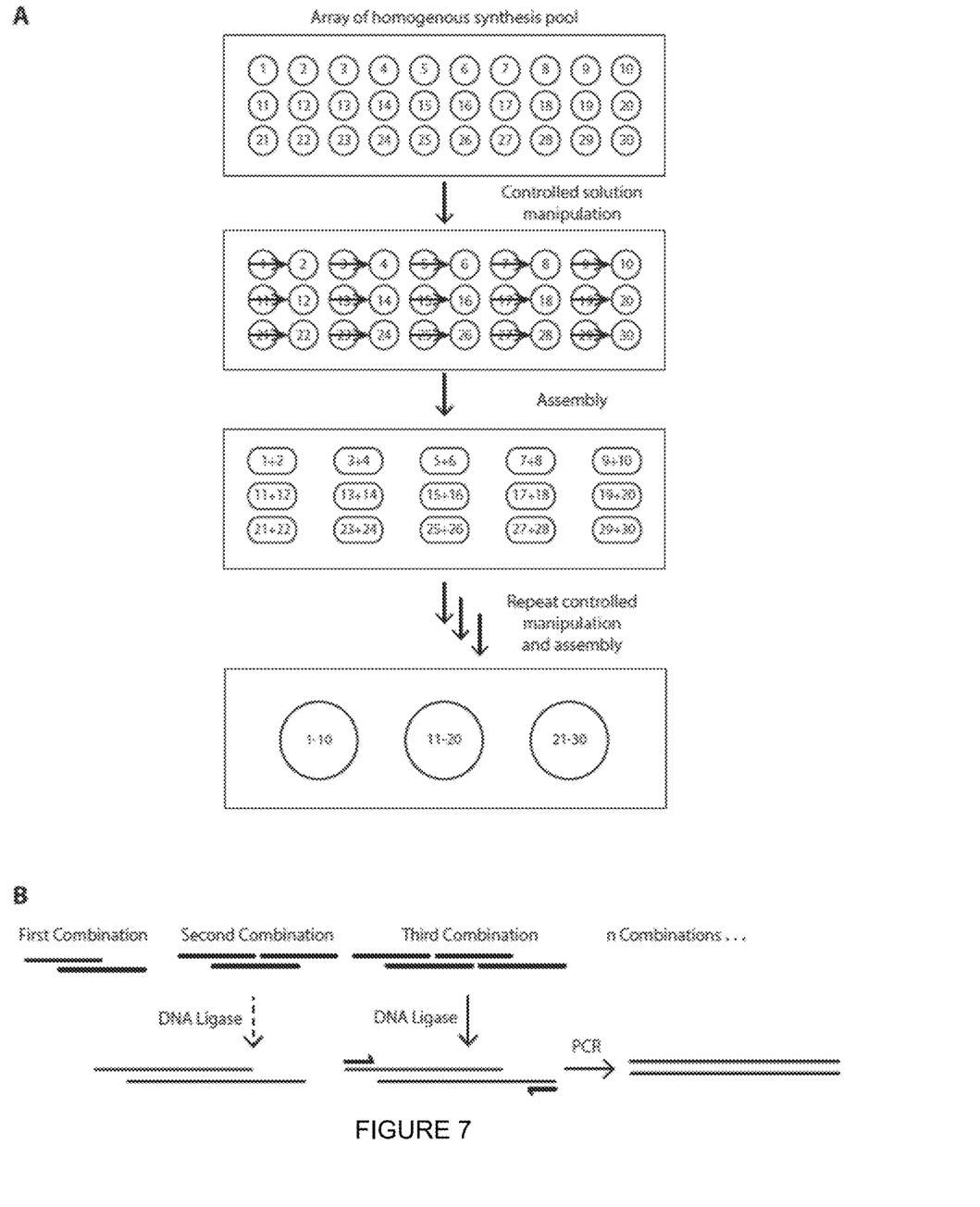
FIG. 7: Schematic on nucleic acid assembly for enzymatic de novo DNA synthesis.

Subsequent Nucleic Acid Assembly (FIG. 7)

8. After step (7) of the last cycle of de novo nucleic acid synthesis, each solution containing a unique and homogenous population of nucleic acid molecules is moved to defined locations on the patterned surface that do not contain immobilized dNTP/NTPs.
9. If the desired nucleic acid product is a pool of oligos without further assembly, the solutions from step (8) can be recovered as individual homogenous populations, or combined either in one pool or in combinations of multiple pools to create unique and heterogenous oligo populations within each pool.
10. If further assembly of oligos is required (e.g., to form longer nucleic acid fragments), all initiator strands will contain a 3' deoxyuridylic acid near the 5'-terminus. Additionally, all oligo constructs can be designed to form overlaps or sequential flush sticky ends upon hybridization. In this step, the solution containing the farthest 3' oligo will be mixed with a mixture to remove the uracil base and cleave the subsequent abasic site to yield a 5'-phosphorylated DNA fragment. Such a solution could contain (1) uracil DNA glycosylase (UDG) and (2) a primary amine.
11. Subsequently, the solution that contains the second farthest oligo from the 3' end will be combined with the solution from step (10).
12. Subsequently, the solution that contains the third farthest oligo will be introduced to the solution from step (10).
13. Subsequently, the solution that contains the nth farthest oligo will be introduced to the solution from step (10) until all desired fragments are hybridized together.
14. Steps (10-14) could also be performed with sequential combination of oligos from the 5' end of the desired longer fragment.
15. DNA ligase (e.g., T4) is introduced to the solution(s) created from steps (10-14), which subsequently ligates all nicks within the newly formed hybridized construct.
16. Optionally, the solution(s) from step (15) can be combined with one or more longer nucleic acid fragment with complementary sticky ends (e.g., a vector backbone).
17. The solution(s) created from steps 10-16 is harvested from the device for further processing.

Process Variant 1

Figure 4:
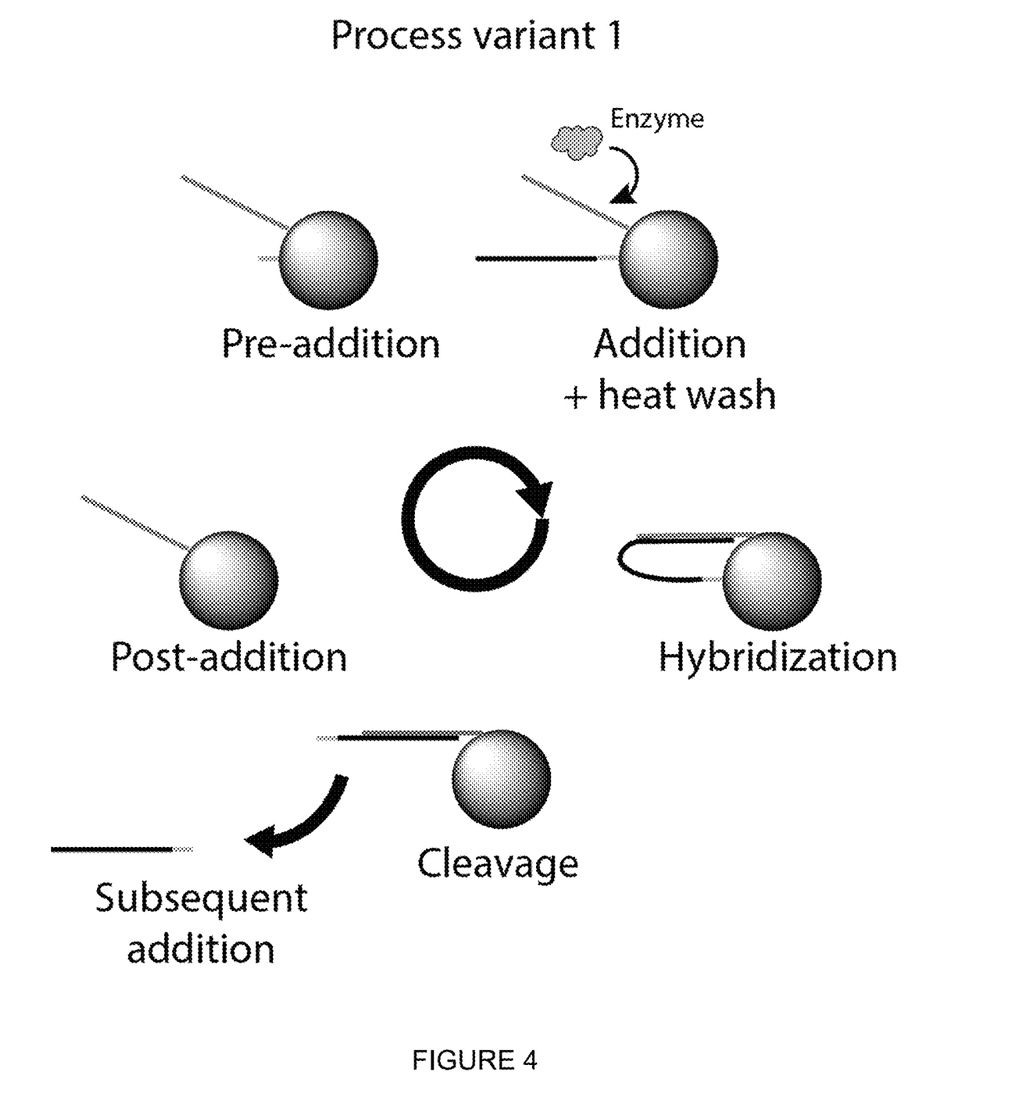
FIG. 4: Enzyme-based alternating-phase synthesis schematic describing process variant 1.

One embodiment of the alternating-phase nucleic acid synthesis process described herein as the second aspect of the invention is referred to herein as "process variant 1," which is described in FIG. 4. In general, this variant to the process relates to the inclusion of a trap strand which is immobilised to the same support moiety as the dNTP/NTP.

Therefore, in one embodiment of the second aspect of the invention, the method additionally comprises providing a nucleic acid trap strand sequence which is complimentary to, and capable of hybridising to, the initiator nucleic acid sequence, wherein said trap strand is immobilised at the 3'-end to the same support moiety as the dNTP/NTP in step (a).

Thus, according to a third aspect of the invention, there is provided a nucleic acid synthesis method which comprises the steps of:

(a) providing a deoxynucleotide triphosphate (dNTP) or nucleotide triphosphate (NTP) immobilised to a support moiety via a cleavable linker;

(b) providing an initiator nucleic acid sequence of length (N);

(c) providing a nucleic acid trap strand sequence which is complimentary to, and capable of hybridising to, the initiator nucleic acid sequence, wherein said trap strand is immobilised at the 3'-end to the same support moiety as the dNTP/NTP in step (a);

(d) adding a nucleic acid synthesis catalyst to couple the initiator nucleic acid sequence to the immobilised dNTP/NTP to create an immobilised, coupled sequence of length (N+1);

(e) providing a reaction temperature greater than the melting temperature of any trap strand/initiator sequence duplexes;

(f) removing any uncoupled initiator nucleic acid sequences;

(g) providing a reaction temperature lower than the melting temperature of any trap strand/initiator sequence duplexes;

(h) cleaving the immobilised, coupled sequence of length (N+1) from the support moiety; and (i) providing a reaction temperature greater than the melting temperature of any trap strand/initiator sequence duplexes to separate the trap strand/initiator sequence duplexes.

It will be appreciated that greater than one dNTP/NTP may be added by providing the product of step (i) to an additional support moiety having immobilised thereon a required deoxynucleotide triphosphate (dNTP) or nucleotide triphosphate (NTP) and an immobilised trap strand and then repeating steps (d) and (i) until a nucleic acid of desired length is synthesised.

It will also be appreciated that the 5' end of the initiator nucleic acid sequence may hybridize to the trap strand to form a duplex. In one embodiment, the duplex is at least 10, 20 or 30 base pairs in length.

Additionally or alternatively, the catalyst in step (d) adds the immobilised dNTP/NTP to the 3' end of the initiator nucleic acid sequence.

In one embodiment, the temperature provided in steps (e) and (i) is selected to prevent the formation of duplexes, such a temperature will suitably be approximately 95° C.

In one embodiment, the removing in step (f) comprises a washing step. Such a washing step serves the purpose of providing an error correction step by removing all unbound initiator nucleic acid sequences. In a further embodiment, step (f) is conducted at the same temperature as step (e).

In one embodiment, the temperature provided in step (g) is selected to allow the formation of duplexes via hybridisation.

In one embodiment, the cleaving in step (h) comprises light, pH, temperature, voltage and the like. In a further embodiment, the cleaving in step (h) comprises a cleavage agent selected from a reducing agent (i.e. TCEP) or a specific pH buffer. Such a cleavage agent cleaves the cleavable linker connecting the 3' end of the coupled sequence of length (N+1) from the support moiety. In one embodiment, the temperature provided in step (h) is any temperature below the melting temperature of any trap strand/initiator sequence duplexes in order to facilitate cleavage.

In one embodiment, following cleavage in step (h), a washing step may be performed in order to remove any leftover cleavage agent.

Figure 5:
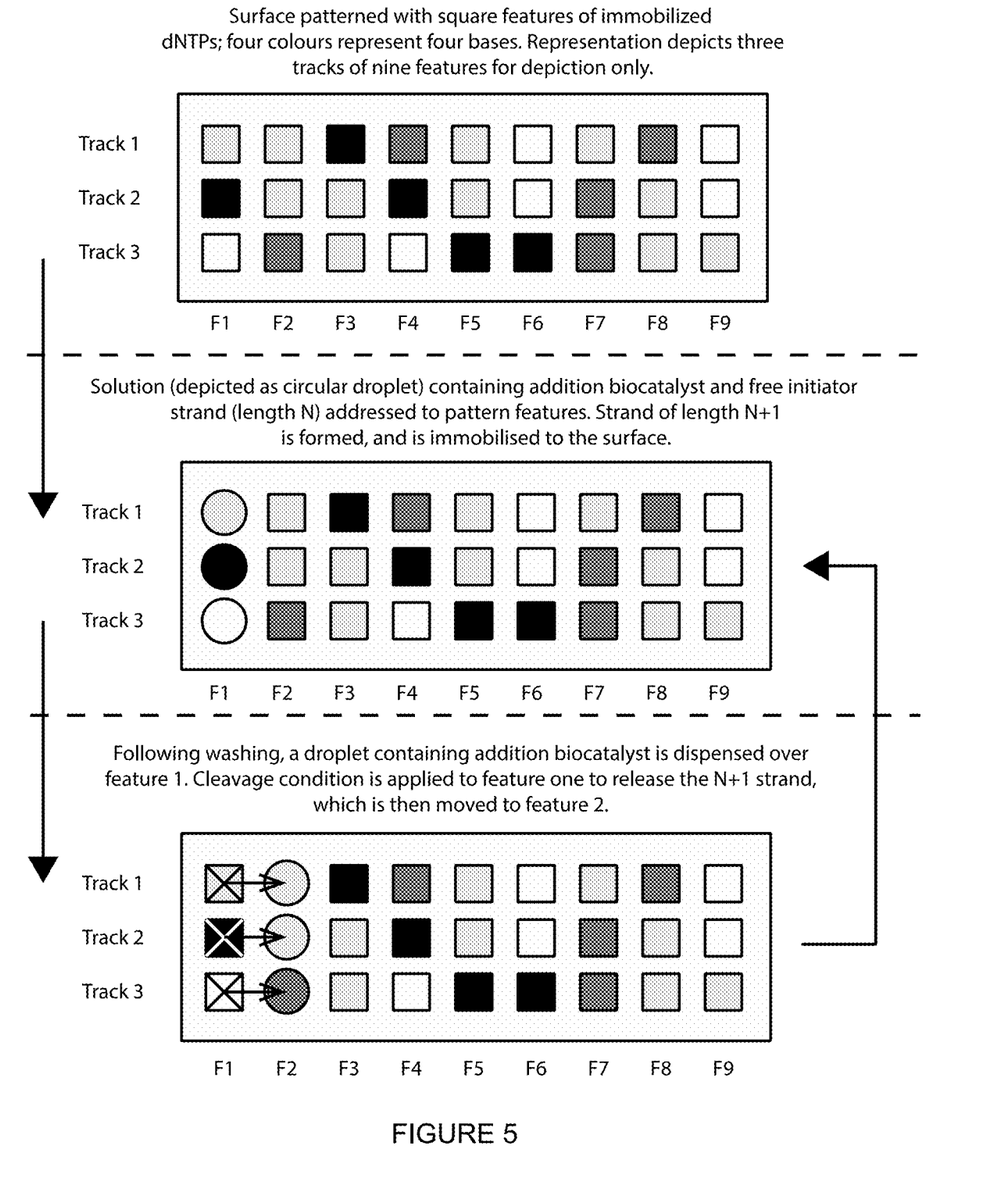
FIG. 5: Example of droplet movement scheme for enzymatic process variant 1. Droplets carrying the initiator strand can be moved over defined tracks of immobilized dNTPs/NTPs through a variety of methods including electrowetting.

Example protocols of how the method of the third aspect of the invention may be performed are described as follows and may be seen in FIGS. 4, 5, and 7:

Immobilized dNTP/NTP De Novo Nucleic Acid Alternating-Phase Synthesis with Bridge Synthesis 1. A support moiety (e.g., a surface) is patterned (e.g., directly functionalized or by printing solid phase particles) with immobilized dNTP/NTPs in a manner so that the position of each feature of the pattern corresponds to a known nitrogenous base identity of that dNTP/NTP (e.g., dATP/ATP or dTTP/UTP or dCTP/CTP or dGTP/GTP).

2. The 3'-end of a strand in part or fully complementary to the initiator strand is immobilized in the same pixels that contain the immobilized dNTP/NTPs. This 3' immobilized strand complementary to the initiator strand is hereby referred to as the trap strand. The dNTP/NTPs and the trap strand are both immobilized on the same surface.

3. A solution containing addition biocatalyst, (e.g., terminal deoxynucleotidyl transferase (TdT) or poly (U) polymerase) and free initiator strands is addressed to each location on the patterned surface.

4. (A) The 5'-end of the complementary strand hybridizes to the trap strand to form a duplex. (B) The addition biocatalyst adds the immobilized dNTP/NTP to the 3'-end of the initiator strand to grow the initiator strand by one nucleotide in the 3' direction (herein referred to as the N+1 species). (A) and (B) do not necessarily proceed in this order; (A) may not occur at all. The N+1 species is terminated from further addition by virtue of immobilization as a result of the 3'-addition of an immobilized dNTP/NTP by the biocatalyst.

5. The reaction surface temperature is elevated above the melting temperature of the hybridized trap-initiator duplex (e.g., 95° C.).

6. Each position containing immobilized N+1 species on the support moiety is addressed with a series of wash solutions (greater than or equal to 1 time) to remove any uncoupled initiator strands from the oligo population. This step is performed at the temperature from step (5).

7. The reaction surface temperature is reduced to below the melting temperature of the trap-initiator duplex allowing hybridization to occur.

8. Each immobilized N+1 species position on the support moiety is addressed with a solution containing a cleavage agent (e.g., a reducing agent such as TCEP, a specific pH buffer, etc.) to cleave the cleavable linker connecting the 3' end of the N+1 immobilized species to the support moiety. The temperature may be elevated but not above the melting temperature of the hybridized trap-initiator duplex in order to facilitate cleavage.

9. Each position containing immobilized N+1 species on the support moiety is addressed with a series of wash solutions (greater than or equal to 1 time) to remove any leftover cleavage agent.

10. The reaction surface temperature is elevated above the melting temperature of the hybridized trap-initiator duplex (e.g., 95° C.) with the last of the series of wash solutions from step (9) and the solution is moved to the next immobilized dNTP/NTP position on the support moiety. Denaturing/chaotropic agents may be present in this step.

11. The addition biocatalyst is then individually addressed to each location on the patterned support moiety containing the solutions from step (10).

12. If continuing de novo nucleic acid synthesis, the process moves to step (13). If terminating de novo nucleic acid synthesis, the process moves to step (14).

13. The addition biocatalyst and cleaved N+1 species are moved to a subsequent location that has not been exposed to solution from step (3). Steps (4)-(13) are repeated until desired sequence is achieved. In this manner, the initiator sequence will have a unique sequence dependent on the positions that the solution from steps (3) and (10) are addressed to.

Subsequent Nucleic Acid Assembly (FIG. 7)

14. After step (10) of the last cycle of de novo nucleic acid synthesis, each solution containing a unique and homogenous population of nucleic acid molecules is moved to defined locations on the patterned support moiety that do not contain immobilized dNTP/NTPs.

15. If the desired nucleic acid product is a pool of oligos without further assembly, the solutions from step (10) can be recovered as individual homogenous populations, or combined either in one pool or in combinations of multiple pools to create unique and heterogenous oligo populations within each pool.

16. If further assembly of oligos is required (e.g., to form longer nucleic acid fragments), all initiator strands will contain a deoxyuridylic acid near the 5'-terminus. Additionally, all oligo constructs can be designed to form overlaps or sequential flush sticky ends upon hybridization. Upon the start of step (10), the solution containing the farthest 3' oligo will be mixed with a mixture to remove the uracil base and cleave the subsequent abasic site to yield a 5'-phosphorylated DNA fragment. Such a solution could contain (1) uracil DNA glycosylase (UDG) and (2) a primary amine.
17. Subsequently, the solution that contains the second farthest oligo from the 3' end will be combined with the solution from step (16).
18. Subsequently, the solution that contains the third farthest oligo will be introduced to the solution from step (16).
19. Subsequently, the solution that contains the nth farthest oligo will be introduced to the solution from step (16) until all desired fragments are hybridized together.
20. Steps (14-19) could also be performed with sequential combination of oligos from the 5' end of the desired longer fragment.
21. DNA ligase (e.g., T4) is introduced to the solution(s) created from steps (14-20), which subsequently ligates all nicks within the newly formed hybridized construct.
22. Optionally, the solution(s) from step (21) can be combined with one or more longer nucleic acid fragment with matching sticky ends (e.g., a vector backbone to form a circular plasmid).
23. The solution(s) created from steps 14-21 is harvested from the device for further processing.

Process Variant 2

Figure 6:
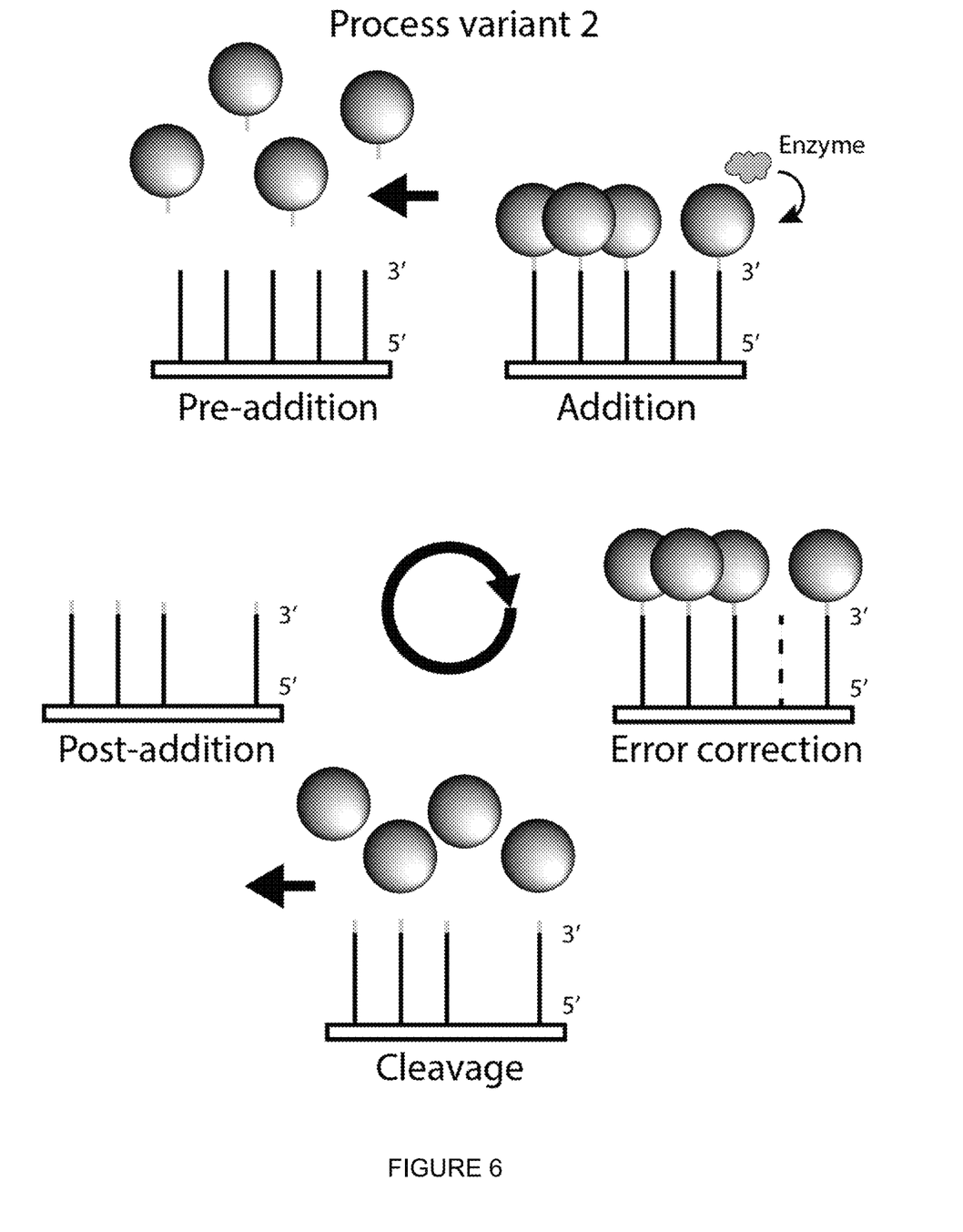
FIG. 6: Enzyme-based alternating-phase synthesis schematic describing process variant 2.

A further embodiment to the alternating-phase nucleic acid synthesis process described herein as the second aspect of the invention is referred to herein as "process variant 2," which is described in FIG. 6. In general, this variant to the process relates to the fact that the dNTP/NTP is immobilized to a mobile phase support moiety and the initiator nucleic acid sequence is immobilised to a solid phase support moiety.

Therefore, in one embodiment of the second aspect of the invention, the method additionally comprises providing the dNTP/NTP immobilised to a mobile phase support moiety via a cleavable linker and an initiator nucleic acid sequence of length (N) immobilised to a solid phase support moiety via a cleavable linker.

Thus, according to a fourth aspect of the invention, there is provided a nucleic acid synthesis method which comprises the steps of:
 (a) providing a deoxynucleotide triphosphate (dNTP) or nucleotide triphosphate (NTP) immobilised to a mobile phase support moiety via a cleavable linker;
 (b) providing an initiator nucleic acid sequence of length (N) immobilised to a solid phase support moiety via a cleavable linker;
 (c) adding a nucleic acid synthesis catalyst to couple the mobile phase immobilised dNTP/NTP to the solid phase immobilised initiator nucleic acid sequence to create an immobilised, coupled sequence of length (N+1);
 (d) removing any uncoupled initiator nucleic acid sequences; and
 (e) cleaving the mobile phase support moiety from the immobilised, coupled sequence of length (N+1).

It will be appreciated that greater than one dNTP/NTP may be added by providing the product of step (e) to an additional deoxynucleotide triphosphate (dNTP) or nucleotide triphosphate (NTP) immobilised to a mobile phase support moiety and then repeating steps (b) and (e) until a nucleic acid of desired length is synthesised.

In one embodiment, the solid phase support moiety comprises the base of a reaction well and the mobile phase support moiety comprises a bead in solution phase within said reaction well.

In one embodiment, the 5' end of the initiator nucleic acid sequence is immobilised to the solid phase support moiety and the 3' end is free from the surface.

In one embodiment, following addition of the nucleic acid synthesis catalyst in step (c), an exonuclease, such as a 3'-5' exonuclease (e.g. exonuclease I from *E. coli*) may be added. This step provides the advantage of degrading any N species which remain as an error correction step to prevent deletions or mutations.

In one embodiment, the cleaving in step (e) comprises light, pH, temperature, voltage and the like. In a further embodiment, the cleaving in step (h) comprises a cleavage agent selected from a reducing agent (i.e. TCEP), light, heat or a specific pH buffer.

In one embodiment, following the cleaving step (e) a washing step is performed. Such a washing step serves the purpose of removing all solutions used in the previous steps.

Example protocols of how the method of the fourth aspect of the invention may be performed are described as follows and may be seen in FIGS. 6 and 7:

Immobilized Mobile-Phase dNTP/NTP De Novo Nucleic Acid Alternating Phase Synthesis with Immobilized Solid-Phase Initiator Strand 1. A solid-phase support moiety is patterned (e.g., directly functionalized or printed solid phase particles) with an initiator strand (of length N) so that the 5'-end is immobilized to the solid-phase support moiety and the 3'-end is free from the solid-phase support moiety.
2. A solution containing biocatalyst (e.g., terminal deoxynucleotidyl transferase (TdT) or poly (U) polymerase) and dNTPs/NTPs immobilized to a mobile-phase support moiety by a cleavable linker is addressed to the locations on the aforementioned patterned surface. Each individually addressed solution has a specific dNTP/NTP (e.g., dATP, dCTP, dTTP, or dGTP) or a combination of dNTPs/NTPs (e.g., dATP, dCTP, dTTP, and dGTP) to achieve sequence control in the growth of the initiator strand. This step subsequently creates an immobilized N+1* species, where the * denotes that the immobilized N+1 species is bound to a mobile-phase support moiety at the 3'-end in addition to being immobilized to the solid-phase support moiety.
3. Each position containing immobilized N+1* species or the entire reaction surface may be introduced to a 3'-5' exonuclease (e.g., exonuclease I from *E. coli*) to degrade any N species remaining as an error correction step to prevent deletions or mutations.
4. Each position containing immobilized N+1* species or the entire solid-phase support moiety is introduced to a solution or a condition (e.g., reducing conditions, irradiation, heat, pH) that cleaves the cleavable linker binding the uncoupled dNTP/NTP and N+1* species to the mobile-phase support moiety.
5. Each position containing immobilized N+1 species or the entire solid-phase support moiety is introduced with one or more wash solutions (greater than or equal to 1 time) to remove any solutions from steps 2-4.

6. Steps 2-5 are repeated until the desired sequence is achieved at each of the positions containing immobilized N+X species, where X is the length of the desired sequence.
7. If the last nucleotide of the initiator strand is a U, then the newly synthesised fragment X may be cleaved away from the original initiator sequence. An example U cleavage cocktail could contain Uracil-DNA glycosylase (UDG) and a primary amine. This step can be performed on the entirety of the solid-phase support moiety or selectively at each immobilized N+X species position. If the latter, the result is a series of solutions individually containing $X_1$, $X_2, \ldots, X_a$, where a is the number of unique sequences synthesized on the reaction surface. Each $X_a$ may have a unique sequence.
8. Subsequent nucleic acid assembly (FIG. 7):
   a. If the desired nucleic acid product is one or more pools of oligonucleotides (i.e., $X_1, X_2, \ldots, X_a$ combined) without further assembly, the solutions from step (7) can be combined either in one pool or in combinations of multiple pools to create unique oligo populations within each pool.
   b. Alternatively, if further assembly of oligos is required (e.g., to form longer nucleic acid fragments), all initiator strands will contain a 5' phosphate following the step (7) U cleavage. Additionally, all oligo constructs will be designed for optimal assembly, for instance, so as to form sequential flush sticky ends upon hybridization.
9. Following step (8b) the solutions that contain the oligo (ODN1) matching the sequence of 3' end of the final assembled nucleic acid product (or any oligo in the case the final assembled product is a circular nucleic acid species) will be combined with the solution that contains a complementary oligo (ODN2).
10. Subsequently, the solution that contains the next overlapping oligo (ODN3) will be introduced to the solution from step (9).
11. Subsequently, the solution that contains the nth farthest oligo (ODNn) will be introduced to the solution from step (10) until all desired fragments are hybridized together.
12. Optionally, the solution from step (11) can be combined with a longer nucleic acid fragment with matching sticky ends (e.g., a vector backbone).
13. DNA ligase (e.g., T4 DNA Ligase) is introduced to the solution from step (11 or 12), which subsequently ligates all nicks within the newly formed hybridized construct.
14. The solution from step 13 is harvested from the device for further processing.

dNTP/NTPs

References herein to 'deoxynucleotide triphosphate (dNTP)' refer to a molecule containing a nucleoside (i.e. a base attached to a deoxyribose or ribose sugar molecule) bound to three phosphate groups. Examples of nucleotide triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of "nucleotide triphosphates (NTPs) that contain ribose are: adenosine triphosphate (ATP), guanosine triphosphate (GTP), cytidine triphosphate (CTP) or uridine triphosphate (UTP). Other types of nucleosides may be bound to three phosphates to form nucleotide triphosphates, such as naturally occurring modified nucleosides and artificial nucleosides.

Support Moieties

It will be appreciated that the support moiety will either comprise a solid phase support moiety or a mobile phase support moiety. It will also be appreciated that the solid phase support moiety or mobile phase support moiety for the dNTP/NTP and/or initiator nucleic acid sequence to be immobilised will be selected from any suitable substrate capable of allowing a dNTP/NTP and/or initiator nucleic acid sequence to be immobilised. Solid phase support moieties typically comprise a surface, material, or particle that remains stationary during the entirety of the synthesis process. Mobile phase support moieties (e.g., particles, beads, nanomaterials, etc.) typically comprise a surface, material, or bead greater than or equal to 1 nm in size, such as 1-1000 nm, in particular 1-100 nm, especially ≥2 nm, ≥3 nm, ≥5 nm or ≥10 nm, that may be mobile or stationary during different portions of the synthesis process.

Examples of suitable solid/mobile phase support moieties may be selected from: a solid surface, (e.g., glass, silicon, gold, plastic etc.), such as a flat surface in particular a 96/384-well plate or a hydrophobic substrate (such as Teflon); a particle, bead, nanoparticle, and/or nanobead including quantum dots (e.g., CdSeS/ZnS, InP/ZnS, and/or CuInS2ZnS), magnetic particles (e.g., iron oxide), metal/metalloid/metal alloy particles (e.g., gold, silver, and/or selenium), metal oxide particles (e.g., oxides of Al, Mg, Zr, Ce, Ti, Zn, Fe, Sn), silica particles, agarose particles, polystyrene particles, carbon-based, i.e. organic, particles (e.g., graphene and/or graphene oxide, nucleic acids, proteins and carbohydrates); and any aforementioned surface, particle, bead, nanoparticle, and/or nanobead that is functionalized or passivated (e.g., with polyethylene glycol, gold, etc.), each of which may be ≥1 nm, such as 1-1000 nm, in particular 1-100 nm, especially ≥1 nm, ≥2 nm, ≥3 nm, ≥5 nm or ≥10 nm in any dimension.

In one embodiment, the solid phase support moiety is selected from a solid surface (e.g., glass, silicon, gold, plastic etc.), such as a flat surface in particular a 96/384-well plate or a hydrophobic substrate (such as Teflon); a solid phase particle, a polymer, and a membrane.

In one embodiment, the mobile phase support moiety is selected from: a mobile phase particle, nanoparticle, ultrafine particle, nanomaterial, or any other material greater than or equal to 1 nm in size, such as 1-1000 nm, in particular 1-100 nm, especially ≥1 nm, ≥2 nm, ≥3 nm, ≥5 nm or ≥10 nm. When using the terms nanoparticle, ultrafine particle, or nanomaterial, they apply to both soluble and insoluble particles.

Examples of suitable polymers may be selected from: polyethylene glycols and polyethylene oxides of any molecular weight; natural polymers and biopolymers of any molecular weight (e.g., dextran, cellulose, collagen, lignins, polyamino acids, chitosan/chitin, nucleic acids, and/or any other carbohydrate or starches); biodegradable polymers (e.g., polylactide, polyglycolide, polyphosphoesters, caprolactone, etc.); Pi-conjugated polymers (e.g., cyano-polyphenylene vinylene, polyaniline, polyfluorenes, poly(fluorine vinylenes), polypyridines, etc.); hydrophilic polymers (e.g., poly(vinyl alcohol), poly(acrylic acid), polyvinylpyrrolidone, poly(2-oxazoline), etc.); polysiloxane polymers; hydrophobic polymers (e.g., styrenes, olefins, esters, ethers, carbonates, etc.); and any aforementioned polymer that is functionalized with a chemical or biochemical moiety allowing for covalent or noncovalent attachment of molecules.

Examples of suitable membranes may be selected from: a lipid bilayer; a lipid monolayer; a vesicle or micelle; a membrane formed by polymers (e.g., cellulose-based, polyvinylidene fluoride, etc.); and any aforementioned membrane that is functionalized with a chemical or biochemical moiety allowing for covalent or noncovalent attachment of molecules.

In one embodiment, the support moiety (i.e. the mobile phase support moiety) comprises a spherical or globular particle which is ≥1 nm in diameter. In a further embodiment, the support moiety comprises a spherical or globular particle which is 1-1000 nm, such as 1-100 nm, in particular ≥1 nm, ≥2 nm, ≥3 nm, ≥5 nm or ≥10 nm in diameter.

In an alternative embodiment, the support moiety (i.e. the mobile phase support moiety) comprises a rod or rod-like particle which is ≥1 nm in any dimension. In a further embodiment, the support moiety comprises a rod or rod-like particle which is 1-1000 nm, such as 1-100 nm, in particular ≥1 nm, ≥2 nm, ≥3 nm, ≥5 nm or ≥10 nm in any dimension.

In an alternative embodiment, the support moiety (i.e. the mobile phase support moiety) comprises a flat structure such as a surface which is ≥1 nm in any dimension. In a further embodiment, the support moiety comprises a flat structure such as a surface which is 1-1000 nm, such as 1-100 nm, in particular ≥1 nm, ≥2 nm, ≥3 nm, ≥5 nm or ≥10 nm in any dimension.

In one embodiment, the support moiety (i.e. the mobile phase support moiety) has a molecular weight>1,000 Da, such as >5,000, in particular, >10,000 Da, especially >25,000 Da.

In one embodiment, the dNTP/NTP is immobilized on a solid phase particle or immobilized by depositing directly onto the surface where nucleic acid synthesis will occur. If the dNTP/NTP is immobilized on a solid phase particle, the solid phase particle will be immobilized onto the surface where nucleic acid synthesis will occur. Alternatively, the solid phase particle may be first immobilized on the surface where nucleic acid synthesis will occur. The dNTP/NTP is then immobilized onto the solid phase particle. In an alternative embodiment, the dNTP/NTP is immobilized on a mobile phase particle. The dNTP/NTP immobilized on a mobile phase particle is subsequently immobilized to a solid phase support moiety following addition to an initiator strand immobilized to a solid phase support moiety as per the process described in process variant 2.

In one embodiment the method of immobilization of solid phase particles is magnetic.

In one embodiment, the dNTP/NTP is immobilized to the solid phase support via the nitrogenous base (i.e. purine or pyrimidine moiety) or the triphosphate moiety or the sugar moiety.

In a further embodiment, the immobilisation comprises an azide-alkyne 1,3-dipolar cycloaddition, a tetrazine/alkene-based cycloaddition, a gold-sulfur bond, a nucleophilic addition of an amine to an epoxide group, a biotin-streptavidin/avidin interaction, the Michael addition of a sulfhydryl group to a Michael acceptor (e.g., maleimide), the oxidation of two sulfhydryl groups to form a disulfide bond, an antibody-antigen interaction (e.g., digoxigenin-anti-digoxigenin), etc.

It will be understood that the immobilization linker contains a cleavable linker. Thus, in one embodiment, immobilization is reversible and/or cleavable.

In one embodiment, the cleavable linker is capable of being cleaved by electromagnetic radiation (e.g., 350 nm light) or a reducing agent or an oxidizing agent or heat or electrochemical or a combination thereof.

In one embodiment, the 5' immobilized strand (i.e., the trap strand) contains a functional group, such as an azido group, capable of linking the strand on the 5'-end to the solid support surface.

Cleavable Linkers

It will be appreciated that a cleavable linker is a broadly stable moiety that connects two or more units. However, upon exposure to the cleavage condition the linker is disrupted, and thus separation of the two units connected by the linker occurs. To offer utility, the cleavage condition must be compatible with the system of interest. There are many chemically cleavable linkers available in the art. Some suitable non-limiting examples include:

A linker comprising an azide masked hemiaminal ether sites (—OCHN$_3$—), which may be cleaved by an azide to amine reduction, triggering a spontaneous breakdown of the revealed hemiaminal ether. Suitable reducing agents include phosphines (e.g., TCEP), thiols (e.g., DTT, EDT) and metal-ligand complexes, including organometallic Ru—, Ir—, Cr—, Rh— and Co— complexes. An example of a suitable metal-ligand complexes is organometallic (Ru(bpy)3 2+) and salts thereof, including Ru(bpy)$_3$Cl$_2$.

Other compositions for protected hemiaminal ethers include allyl or allyl carbamate moieties, which may be cleaved using transition metals complexed with water soluble ligands, e.g., Pd with water soluble phosphine ligands); sulfmoc, which may be cleaved with a mild base, e.g. 1% Na$_2$CO$_3$; m-chloro-p-acyloxybenzyl carbamate, which may be cleaved with mild base, e.g.: 0.1 M NaOH; and 4-azidobenzyl carbamate, which may be cleaved with reducing agents, e.g.: TCEP, DTT).

A linker comprising a phosphine moiety, which may be cleaved through incubation with azide reagents, for example alkyl or aryl azides. The aza-ylid generated may react with a suitably positioned ester moiety to facilitate cleavage.

A linker comprising a silicon containing site, which may be cleaved in the presence of fluoride ions, such as KF and tetra-n-butylammonium fluoride (TBAF).

A linker comprising a disulfide site, which may be cleaved by reduction with phosphine or thiol reagents.

A linker comprising a cyanoethyl site, which may be cleaved under basic conditions, such as solutions of NH$_3$ or 10% K$_2$CO$_3$.

A linker comprising a photocleavable site, which may be cleaved by UV light, ideally of a wavelength orthogonal to the system of interest. Suitable photocleavable sites are well known in the art. For example, an orthonitrobenzyl group may be cleaved by UV at 365 nm.

Other suitable cleavage sites are well known in the art.

Initiator Nucleic Acid Sequences

References herein to an 'initiator nucleic acid sequence' refer to a short oligonucleotide with a free 3'-end which the immobilised dNTP or NTP can be attached to. In one embodiment, the initiator sequence is a DNA initiator sequence. In an alternative embodiment, the initiator sequence is an RNA initiator sequence.

References herein to a 'DNA initiator sequence' refer to a small sequence of DNA which the immobilised dNTP or NTP can be attached to, i.e. DNA will be synthesised from the end of the DNA initiator sequence.

In one embodiment, the initiator nucleic acid sequence contains a defined sequence from 1 to X nucleotides, where X is the length of the initiator strand. The defined initiator strand sequence thus becomes a barcode for its unique de novo synthesized sequence. In a further embodiment, the initiator nucleic acid sequence is a defined sequence between 1 and 1000 nucleotides long. In a further embodiment, the initiator nucleic acid sequence is a defined sequence between 10 and 100 nucleotides long. In a further embodiment, the initiator nucleic acid sequence is a defined sequence between 15-50 nucleotides long.

In one embodiment, the initiator nucleic acid sequence has a sequence 5'-NNNN . . . NNNN-3', where N represents any nucleotide. In an alternative embodiment, the initiator nucleic acid sequence may have a sequence 5'-NNNN . . . NNNNU-3', where N represents any nucleotide and U represents deoxyuridylic acid.

In one embodiment, the initiator sequence is single-stranded. In an alternative embodiment, the initiator sequence is double-stranded. It will be understood by persons skilled in the art that a 3'-overhang (i.e., a free 3'-end) allows for efficient addition.

In one embodiment, the initiator nucleic acid sequence is in solution phase (as in the second and third aspects of the invention). In an alternative embodiment, the initiator nucleic acid sequence is immobilised to a solid phase support moiety (as in the fourth aspect of the invention). It will be appreciated that when the initiator nucleic acid sequence is immobilised to a solid phase support moiety it will either be immobilised to the same support moiety as the immobilised dNTP/NTP or a different support moiety (as in the fourth aspect of the invention).

Nucleic Acid Synthesis Catalysts

In one embodiment, the nucleic acid synthesis catalyst comprises any suitable enzyme capable of performing nucleic acid synthesis.

In a further embodiment, the nucleic acid synthesis catalyst comprises any suitable transferase or polymerase capable of performing nucleic acid synthesis.

In general, the nucleic acid synthesis catalyst catalyses the formation of a covalent bond between the 3' terminus of the initiator nucleic acid sequence and the immobilised dNTP/NTP resulting in growth of the initiator nucleic acid sequence by one nucleotide in the 3' direction (i.e. formation of an N+1 species).

In a further embodiment, the nucleic acid synthesis catalyst is selected from: a terminal deoxynucleotidyl transferase (TdT), poly (U) polymerase, poly (A) polymerase, and polymerase theta (PolQ).

In a further embodiment, the nucleic acid synthesis catalyst is selected from: any non-natural, recombinant, and/or engineered terminal deoxynucleotidyl transferase (TdT), poly (U) polymerase, poly (A) polymerase, and polymerase theta (PolQ).

In a further embodiment, the nucleic acid synthesis catalyst is selected from: terminal deoxynucleotidyl transferase (TdT) and any non-natural, recombinant, and/or engineered terminal deoxynucleotidyl transferase (TdT).

References herein to "TdT" refer to a terminal deoxynucleotidyl transferase (TdT) enzyme and include references to purified and recombinant forms of said enzyme. TdT is also commonly known as DNTT (DNA nucleotidylexotransferase) and any such terms should be used interchangeably.

Examples of suitable terminal deoxynucleotidyl transferase (TdT) enzymes are described in WO 2016/128731 (the TdTs of which are herein incorporated by reference).

Examples of suitable polymerase theta (PolQ) enzymes are described in GB Patent Application No. 1613185.6 (the PolQs of which are herein incorporated by reference).

Devices

The methodology of the present invention may be run through many types of devices including a microfluidic device, electrowetting-on-dielectric device, an inkjet device, and/or a column-based device. In a specific example, movement of the initiator nucleic acid sequence between areas of immobilized dNTP/NTP can be achieved by droplet actuation by electrowetting on dielectric (EWOD) for the second and third aspects of the invention. Furthermore, for the fourth aspect of the invention, droplets containing solid phase particles with immobilized dNTP/NTP can be actuated by EWOD. Alternatively, droplet actuation in the second, third and fourth aspects of the invention can be achieved by programmable magnetic forces, temperature gradients, etc.

Immobilised dNTP/NTPs

According to a further aspect of the invention, there is provided an immobilised dNTP/NTP of formula (I):

wherein $R_1$ and $R_2$ independently represent H or OH or a protected derivative thereof;

X represents hydrogen or one or more phosphate groups;

W represents a base;

Y represents a cleavable linker; and

Z represents a support moiety

In one embodiment, X represents a monophosphate, diphosphate, triphosphate or tetraphosphate group.

In one embodiment, W is selected from a nitrogenous base. In a further embodiment, W is selected from a purine or pyrimidine moiety. In a yet further embodiment, the base is selected from adenine, guanine, uracil, thymine or cytosine.

In one embodiment, the support moiety defined as Z is as defined herein.

In a further embodiment, the support moiety additionally comprises a nucleic acid trap strand sequence as defined herein.

According to a further aspect of the invention, there is provided the use of an immobilised dNTP/NTP as defined herein in a nucleic acid synthesis method. In one embodiment, the nucleic acid synthesis method is as defined herein.

Nucleic Acid Synthesis Kits

According to a further aspect of the invention, there is provided a nucleic acid synthesis kit which comprises an immobilised dNTP/NTP as defined herein, an initiator nucleic acid sequence as defined herein, a nucleic acid synthesis catalyst as defined herein and instructions to use said kit in accordance with any of the methods defined herein.

According to a further aspect of the invention, there is provided the use of a nucleic acid synthesis kit which comprises an immobilised dNTP/NTP as defined herein, an initiator nucleic acid sequence as defined herein, a nucleic acid synthesis catalyst as defined herein and instructions to use said kit in accordance with any of the methods defined herein, in a method of nucleic acid synthesis.

In one embodiment, the kit additionally comprises a device as defined herein. In a further embodiment, the kit additionally comprises a microfluidic device, electrowetting-on-dielectric device, an inkjet device, and/or a column-based device.

The invention claimed is:

1. A polymer synthesis method which comprises the steps of:
   (a) providing a monomer immobilised to a support moiety via a cleavable linker, wherein the monomer is a deoxynucleotide triphosphate (dNTP), or a nucleotide triphosphate (NTP);
   (b) providing a polymer having an initiator nucleic acid sequence of length (N);
   (c) providing a nucleic acid synthesis catalyst to couple the initiator nucleic acid sequence to the immobilised monomer to create an immobilised, coupled polymer of length (N+1);
   (d) removing any uncoupled polymers; and
   (e) cleaving the immobilised, coupled polymer of length (N+1) from the support moiety.

2. The method of claim 1, wherein step (d) comprises a washing step.

3. The method of claim 1, wherein the nucleic acid catalyst is an enzyme selected from terminal deoxynucleotidyl transferase (TdT), poly (U) polymerase, poly (A) polymerase, and polymerase theta (PolQ).

4. The method of claim 1, which comprises providing the product of step (e) to an additional deoxynucleotide triphosphate (dNTP) or nucleotide triphosphate (NTP) immobilised to a support moiety and then repeating steps (b) to (e) until a nucleic acid of desired length is synthesised.

5. The method of claim 1, wherein the support moiety is selected from glass, silicon, gold, or plastic.

6. The method of claim 5, wherein the support moiety is selected from: a particle, nanoparticle, ultrafine particle, nanomaterial, membrane, or any other material of 1-1000 nm in size, or of 1-100 nm, or of ≥1 nm, or of ≥2 nm, or of ≥3 nm, or of ≥5 nm, or of ≥10 nm in size.

7. The method of claim 1, wherein the monomer immobilised on the support moiety is a dNTP/NTP of formula (I):

(I)

wherein $R_1$ and $R_2$ independently represent H or OH or a protected derivative thereof;

X represents hydrogen or one or more phosphate groups;

W represents a base;

Y represents a cleavable linker; and

Z represents a support moiety.

8. The method of claim 7, wherein the cleavable linker is selected from: a masked hemiaminal ether site, sulfmoc, m-chloro-p-acyloxybenzyl carbamate and 4-azidobenzyl carbamate; a linker comprising a phosphine moiety; a linker comprising a silicon containing site; a linker comprising a disulfide site; a linker comprising a cyanoethyl site; and a linker comprising a photocleavable site.

9. The method of claim 7, wherein the method is performed on a microfluidic device, electrowetting-on-dielectric device, an inkjet device or other printing platform.

10. The method of claim 9, wherein the device is a electrowetting-on-dielectric device.

11. The method of claim 1, wherein the support moiety is a particle, bead, nanoparticle, or a nanobead.

12. The method of claim 11, wherein the support moiety comprises quantum dots.

13. The method of claim 11, wherein the support moiety comprises magnetic particles.

14. The method of claim 1, wherein the support moiety comprises a metal, metalloid or metal alloy particles, wherein the metal, metalloid or metal alloy particles are selected from gold, silver, and selenium.

15. The method of claim 11, wherein the support moiety comprises metal oxide particles, wherein the metal oxide particles are selected from oxides of Al, Mg, Zr, Ce, Ti, Zn, Fe, and Sn.

16. The method of claim 11, wherein the support moiety comprises silica particles.

17. The method of claim 11, wherein the support moiety is an organic polymer.

18. The method of claim 17, wherein the organic polymer is selected from agarose particles, polystyrene particles, graphene, and graphene oxide.

19. The method of claim 7, wherein the base is a purine or a pyrimidine.

* * * * *